– – –

United States Patent [19]

Arnold

[11] Patent Number: 5,273,574
[45] Date of Patent: Dec. 28, 1993

[54] BOND BETWEEN AMALGAM AND GLASS IONOMER CEMENT

[75] Inventor: Thomas J. Arnold, Winslow, Ind.

[73] Assignee: Mion International Corporation, Winslow, Ind.

[21] Appl. No.: 991,112

[22] Filed: Dec. 16, 1992

Related U.S. Application Data

[63] Continuation-in-part of Ser. No. 942,375, Sep. 9, 1992.

[51] Int. Cl.$^5$ .......................... A61K 6/05; A61K 6/06
[52] U.S. Cl. .................................. 106/35; 433/228.1
[58] Field of Search .............. 106/35; 433/228.1, 38.3; 501/106

[56] References Cited

U.S. PATENT DOCUMENTS

| | | | |
|---|---|---|---|
| Re. 33,100 | 10/1989 | Ibsen et al. | 106/35 |
| 3,676,112 | 7/1972 | Muhler | 75/173 R |
| 3,933,961 | 1/1976 | Burns | 264/111 |
| 4,064,629 | 12/1977 | Stoner et al. | 433/217.1 |
| 4,654,007 | 3/1987 | Sigler et al. | 433/236 |
| 4,684,347 | 8/1987 | Palaghias | 433/228.1 |
| 4,738,722 | 4/1988 | Ibsen et al. | 106/35 |
| 4,775,592 | 10/1988 | Akahane et al. | 428/406 |
| 4,813,871 | 3/1989 | Friedman | 433/90 |
| 4,872,936 | 10/1989 | Engelbrecht | 156/307.3 |

FOREIGN PATENT DOCUMENTS

| | | |
|---|---|---|
| 8103637 | 1/1981 | Japan . |
| 87231668 | 10/1987 | Japan . |
| 2-275731 | 11/1990 | Japan . |

OTHER PUBLICATIONS

Elliott et al, "Physical and Mechanical Properties of Glass–Ionomer Cements", Br. Polym. J., 7(5) 297–306 (Eng.) 1975.

Staninec et al., Bonding of Amalgram to tooth structure: Tensile adhesion and microleakage tests; Journal of Prosthetic Dentistry; 59:4; Apr. 1988; pp. 397–402.

Rueggeberg et al., Bond Strength of Panavia EX to Dental Amalgam; International Journal of Prosthodontics; 2:4; pp. 371–375.

Torii et al., Inhibition in Vitro of Caries around amalgam Restorations by Bonding Amalgam to Tooth Structure; Operative Dentistry; 14; 1989; pp. 142–148.

Shimizu et al., Bond Strength between Amalgam and Tooth Hard Tissues with Application of Fluoride, Glass Ionomer Cement and . . . , Dental Materials Journal; 52; 1986; pp. 225–232.

Varga et al., Bonding of Amalgam Filling to Tooth Cavity with Adhesive Resin; Dental Materials Journal; 5:2; 1986; pp. 158–164.

Lacy et al., The bonded amalgam restoration; Quintessence International; 20:7; 1989, pp. 521–524.

Cooley et al., Bond strength of resin to amalgam as affected by surface finish; Quintessence International; 20:4; pp. 237–239, 1989.

Hibler et al.; Bond Strength Comparisons of Repaired dental Amalgams; Quintessence Intenation; 19:6; 1989; pp. 411–415.

Yu et al., Experimental use of a bonding agent to reduce marginal microleakage in amalgam restorations; Quintessence International; 18:11; 1987; pp. 783, 787.

Colon et al., Les amalgames colles: technique diretc et (List continued on next page.)

Primary Examiner—Mark L. Bell
Assistant Examiner—Margaret Einsmann
Attorney, Agent, or Firm—Baker & Daniels

[57] ABSTRACT

An additive for glass ionomer cement comprising an effective amount of zircon to whiten, decrease the thickness and/or increase the setting time of the glass ionomer cement. The addition of zircon crystals to either the powder component of the liquid component of a glass ionomer cement allows one to control the color, mixability and handling characteristics, and setting time of the cement without adversely effecting the cement's intended functionality, such as the bond strength of the cement. The zircon additive may be utilized in conjunction with other additives and may be used in glass ionomer cements used as restorative materials, a prosthetic device cement, or as a luting agent, base or liner.

10 Claims, No Drawings

OTHER PUBLICATIONS

*indirecte;* Revue D'Odonto Stomatologie; 16:1; 1987; pp. 9–18.

Warren et al., *Bonding amalgam to glass ionomer with PAA;* Dental Materials; 4; 1988; pp. 191–196.

Stevenson, *Modified Bonded Amalgam Technique* (letter to the editor); British Dental Journal; Dec. 24, 1983; p. 401.

*The Government Chemist Plays Host;* British Dental Journal; Apr. 23, 1983; p. 268.

Braen, *The Effect of Technology on Clinical Practice,* Jul. 1 to 3, 1983.

*Effects of Polycarboxylate and Glass-Ionomer cements on Stainless Steel crown Retention;* British Dental Journal; p. 218, 1983.

Pearson, *Finishing of Glass-Ionomer Cements;* British Dental Journal; 155; 1983; pp. 226–228.

*Opacity of Glass-Ionomer Cements,* Acta Odontal Scand 41:155–157, 1983.

Prodger et al., *ASPA Adhesion Study;* British Dental Journal; 143, 1977; pp. 266–274.

*Dentist's Desk Reference;* Materials, Instruments and Equipment; American Dental Association; 1981, pp. Preface and 84–54.

Expansion of the Acceptance Program for dental materials and devices; glass ionomer cements; JADA; 99; Aug. 1979; pp. 227–228.

Reported Sensitivity to glass ionomer luting cements; JADA; 109; Sep. 1984; p. 476.

Status report on the glass ionomer cements; JADA; 99; Aug. 1979; pp. 221–224.

Dentist's Desk Reference; *Materials, Instruments and equipment;* American Dental association; 1983; pp. Preface and 118–119.

Gilmore et al., Operative Dentistry; 1973; pp. 64–95.

Cardosa et al., *Low-Silver amalgam restorations; A two-year clinical evaluation,* Dental Materials, Jul. 1989; 5:277–80.

Osborn, *Clinical Assessment of 14 amalgam alloys, General Dentistry,* May-Jun. 1990:206–208.

Powell et al., *Effect of Admixed Indium on Mercury Vapor Release from Dental Amalgam,* Journal of Dental Research, Aug. 1989; 68(8):123;123.

Mercurial Debata, Science; d55(13):1356–1357, 1992.

Fasbinder et al., *Tensile Bond Strength of Dental Adhesives to Dentin and Enamel,* Dental Materials, Jul. 1989; 5:272–276.

Curtis, *The Use of Dental Amalgam—An Art or a Science?,* Jul./Aug. 1992 Dental Update pp. 239–245.

Watson, *The interfacial region of the tooth/glass ionomer restoration: A confocal optical microscope study,* Am. J. Dent. 1991; 4:303–310.

Amalgambond—The first bonding agent for amalgam, Advertisement, American Dental Assoc. News, 1991; 22.13: p. 28.

Starting today, you may never have to re-cement again . . . ever. Advertisement, Dentistry Today, 199; 10,6: p.17.

Shofu Advertisement, Dental Products Report, Sep. 1991, p. 65.

Dentistry Techniques, Dental Products Report, Sep. 1991, pp. 74–75.

Retentive Pins . . . Are they everything they'3 re cracked up to be?, Advertisement, American Dental Assoc. News, 1991; 22, 14:p. 15.

Aboush et al., An evaluation of the bonding of glass-ionomer restorations to dentine and amalgam, British Dental Journal, 1986;16:179–184.

Gilmore et al., Operative Dentistry, C. V. Mosby Company, 1973; pp. 196–200, 279–281.

Geristore: A Pediatric/Geriatric Restorative, video tape by Dr. Ronald Jordan, American Society for Clinical Research, No. 1006780, V1.0.

New Era of Composite Bonding, Dentistry Today, Jun./Jul. 1991, pp. 32,34.

New Products—Adhesive System, Dental Products Report, Sep. 1991.

Scherer et al., Reinforced Glass Ionomer Cement vs. Zinc Phosphate Cement, 18th Annual Session of Assoc. for Dental Research, San Francisco.

Johnson et al., Dentin Bonding Systems: A Review of Current Products and Techniques, The Journal of the American Dental Assoc., 1991; 122:34–41.

Scherer et al., Visible Light-Activated Glass Ionomer Cement:Use as Liners/Bases and Restorations, PP&A;4(4):27–30, 1992.

Illustrated Dictionary of Dentistry, W. B. Saunders Company, pp. 37–38.

OTHER PUBLICATIONS

Aboush et al., The bonding of glass-ionomer cements to dental amalgam, British Dental Journal, 1989; 166:255-257.

Mojan et al., Maximum Bond Strength of Dental Luting Cement to Amalgam Alloy, Journal of Dental Research, Nov. 1989; 68(11):1545-1549.

Matis, How Finishing Affects Glass Ionomers, Journal of American Dental Association 1991; 122:34-46.

Hotz et al., The Bonding of Glass Ionomer Cements to Metal and Tooth Substrates, British Dental Journal, 1977; 142:41-47.

Sherer et al., Reinforced Glass Ionomer Cement vs. Zinc Phosphate Cement, 18th Annual Session of the American Association for Dental Research, San Francisco, Calif. Jan. 1990.

Stookey et al., Studies Concerning the Polishing Properties of Zirconium Silicate on Enamel, Journal of Peridontal, 1966; 37(3):200-207.

Anderson et al., Effects of Zirconium Silicate Chewing Gum on Plaque and Gingivitis, Quintessence International, 1990;21(6):479-489.

Stookey et al, Studies Concerning the Biological Properties of Zirconium Silicate, Journal of Peridontal, 1967; 38(1):53-63.

Swift et al., Use of Glass Ionomer Cements by Iowa Dentist, General Dentistry, Nov./Dec. 1990;450-453.

Shannon, A Punice-Zirconium Silicate Prophylaxis Paste Containing 2% Stannous Fluoride in Water-Free Solution, Pharmocology and Therapeutics in Dentistry, 1970; 1:24-30.

Fleming et al., Effect on Caries of Self-Application of a Zirconium Silicate Paste Containing 9% Stannous Fluoride, Community Dent. Oral Epidemiol., 1976; 4:142-148.

BOND BETWEEN AMALGAM AND GLASS IONOMER CEMENT

This is a continuation-in-part of application Ser. No. 07/942,375, filed Sep. 9, 1992.

FIELD OF THE INVENTION

This invention relates to cements for use in dental and medical applications, and, in particular, to an improved glass ionomer cement used for dental purposes.

BACKGROUND OF THE INVENTION

Glass ionomer cements have been used for a variety of dental purposes. When introduced, glass ionomer cements were of a consistency rendering them useful as a restorative material. Today, glass ionomer restorative materials are successful in restoring significant lesions. For example, Matis, et al., *How Finishing Affects Glass Ionomers*, Journal of the American Dental Association, 1991; 122:43–46, describes a five year study to determine the effectiveness of restorations involving the use of glass ionomer restorative materials and concluding that glass ionomer restorative is materials are outstanding in their retentive capability.

Studies have been conducted to determine the capability of glass ionomer cement to adhere to various materials, including the tests disclosed in Holtz, et al., *The Bonding of Glass ionomer Cements to Metal and Tooth Substrates*, British Dental Journal, 1977; 142:41–47. This study demonstrated that glass ionomer cement bonds well to dentin and enamel, and also adheres to some cast metals. Adherence to cast metals is most successful when the surface of the metal is first etched with an acid, such as citric acid, before applying the glass ionomer cement as such etching enhances the mechanical bond between the cement and the metal.

Results of studies such as Holtz, et al. have provided a basis for the use of glass ionomer cements for the application of metal and porcelain prostheses. For example, in U.S. Pat. No. 4,654,007, a layer of glass ionomer cement is applied to a tooth prior to attaching a porcelain restoration thereto. After the cement is properly hardened and before the porcelain restoration is bonded with an acrylic cement, the hardened glass ionomer cement is etched to create microscopic surface irregularities which facilitate mechanical retention of the acrylic cement to the glass ionomer cement.

Several years after glass ionomer restorative materials were first made available to dentists, new formulations of glass ionomer cements were developed for use as a luting agents or bases or liners. When used as a base or liner for amalgam restorations, glass ionomer cements are first allowed to harden in the tooth before the amalgam is placed in the tooth on the hardened glass ionomer cement. Studies showed that when the glass ionomer cement was hardened that the glass ionomer cement shrinks, leaving a slight 60-80 um gap between the hardened glass ionomer cement and the hardened amalgam. Scherer, *Reinforced Glass ionomer Cement vs. Zinc Phosphate Cement*, 18th Annual Session of the American Association for Dental Research, San Francisco, California. Thus, hardened glass ionomer cement bases/liners/luting agents do not in and of themselves bond the amalgam to the tooth.

The invention disclosed in U.S. patent application Ser. No. 07/942,375, filed Sep. 9, 1992, the disclosure of which is incorporated herein by reference, comprises a dental restoration system that works well with conventional materials, specifically glass ionomer cement and amalgam, to allow the tooth to be filled instead of being extracted or requiring the application of a prosthesis such as a crown or bridge. Such a system is inexpensive to use and results in an improved bond strength over prior methods without requiring that the glass ionomer cement first be hardened and then acid etched before filling the lesion with amalgam.

Glass ionomer cements, whether used as a restorative material, a cement for a prosthesis such as a bridge or crown, or as a luting agent/base/liner, generally comprise a glass ionomer cement powder which is mixed with a glass ionomer cement liquid. Before application, the powder is mixed with the liquid to form the cement. For all glass ionomer cements, the powder component is generally composed of silica and various oxides and fluorides. For example, the powder component of the glass ionomer Cement disclosed in U.S. Pat. No. Re. 33,100, which is intended for use as a luting agent, base or liner, comprises:

| Percentage | | Composition |
| --- | --- | --- |
| 26% | $SO_2$ | Silica |
| 6% | $B_2O_3$ | Boron Oxide |
| 16% | $Al_2O_3$ | Aluminum Oxide |
| 6% | $AlF_3$ | Aluminum Fluoride |
| 5% | $NH_4F$ | Ammonium Fluoride |
| 4% | $P_2O_5$ | Phosphorus Pentoxide |
| 37% | $CaF_2$ | Calcium Fluoride |

The liquid portion of glass ionomer cement disclosed in U.S. Pat. No. Re. 33,100 comprises:

| | |
| --- | --- |
| 91.5% | Polyacrylic acid of a low molecular weight, 40.0% solution in water |
| 8.5% | D-tartaric acid |

The powder portion of the glass ionomer cement is mixed with the liquid portion in a ratio of 1:1 to 2:1 by weight.

Two other glass ionomer cements intended for use as a luting agent, base or liner, are Ketac-CEM Radiopaque glass ionomer cement distributed by ESPE Premier Sales Corporation of Norristown, Pennsylvania, and GlasIonomer Type I cement distributed by Shofu Dental Corporation of Menlo, California. Glass ionomer restorative materials are understood to be of a similar composition, but there are differences in particle sizes, mix ratios, liquid compositions, and formulations which vary materials from manufacturer to manufacturer.

Numerous variations of the composition of glass ionomer cements have been made in an effort to improve one of more characteristics of the cement. An ideal glass ionomer cement has a pleasant color similar to that of tooth structure, is easily mixed, sets in a controlled manner in a reasonable time frame. To accomplish these objectives, the cement must be chemically reactive to tooth structure, strong and insoluble, and must be biocompatible, not caustic. Various degrees of setting time, color and handling characteristics are desired depending on the particular application of the glass ionomer cement. For example, when used as a cement for a crown, bridge or other prosthesis, the glass ionomer should not set quickly to allow full seating of the prosthesis before the cement hardens. Should the cement be used as a base or liner under an amalgam restoration wherein the cement is first allowed to harden, faster setting times are desirable.

Some known additives to glass ionomer cement to control the cement's handling characteristics, color, and setting times include, for example, zinc oxide as disclosed in U.S. Pat. No. Re. 33,100. Zinc oxide as an additive to glass ionomer cement primarily serves as a buffering agent, neutralizing the acidity of the cement to reduce pulpal irritations. The presence of zinc oxide also increases the rate of setting reaction, results in a rougher surface when etched, and controls the setting reaction time. U.S. Pat. No. Re. 33,100 also discloses titanium dioxide as an additive to glass ionomer cement which further increases the cement's strength, further controls the setting reaction, and changes the color of the cement so that it is readily distinguishable from that of tooth structure.

U.S. Pat. No. 4,775,592 suggests treating the surface of a fluoroaluminosilicate glass powder of a glass ionomer cement with fluoride to improve crushing strength and to result in a fluidity or viscosity of a mixed cement which improves workability or mixability. To treat the glass powder, the fluoride is not simply mixed with the glass powder, but rather conventional treatment techniques are employed. For example, the treatment may involve mixing the fluoride with water, mixing the fluoride-water mixture with the glass powder, and evaporating the water content out of the resulting mixture.

Zirconia (zirconium oxide) has also been used as an additive with glass ionomer cement compositions. Japanese patent no. 2,275,731 (WPI 90-380320/51) discloses a glass ionomer cement to which small percentages of zirconium oxide and zinc oxide have been added to improve the cement's resistance to disintegration and crushing and to improve hardening time.

Each of these additives, zinc oxide, zirconia and fluorides, may chemically react with the glass ionomer cement composition. Potentially, each chemical reaction may adversely affect the cement's functionality. Thus, it is desirable to provide an improved glass ionomer cement comprising the conventional glass ionomer cement formula and additives that are non-reactive to the cement. In this manner, the glass ionomer cement is not significantly modified, since the additive does not chemically react with the cement, so as to diminish the capability of the cement to perform the tasks for which it is intended and for which it is used in current applications.

When the glass ionomer cement is used as a base for an amalgam restoration whereby the cement is first allowed to harden prior to the application of amalgam to the lesion, some manufacturers, as mentioned in U.S. Pat. No. Re. 33,100, have added the silver alloy powder component of an amalgam into the powder component of the glass ionomer cement with the intent of strengthening the cement without affecting the cement's adhesive properties. However, the silver contained in the additive corrodes in the oral environment and can turn the tooth dark. Therefore, it is desirable to provide an additive which is not corrosive in the oral environment.

Zircon, also known as zirconium silicate or zirconium silicon oxide, is currently used as a prophylaxis polishing agent. Stookey, et al., *Studies Concerning the Polishing Properties of Zirconium Silicate on Enamel*, Journal of Peridontal, 1966; 37(3): 200–207. Zirconium silicate has also been added to chewing gum. Anderson, et al., *Effects of Zirconium Silicate Chewing Gum on Plaque and Gingivitis*, Quintessence International, 1990; 21(6):479–489.

Due to its use as a prophylaxis polishing agent, the biological effects of zirconium silicate on various tissues have been studied. Stookey, et al., *Studies Concerning the Biological Properties of Zirconium Silicate*, Journal of Peridontal, 1967; 38(1): 53–63. This study indicated that zirconium silicate, when introduced in modest amounts, is non-toxic. It is noted that the reactions, or lack thereof, caused by zirconium silicate is in contrast to other forms of compositions containing the element zirconium. Specifically, reactions within tissue have been documented for some zirconium salts, such as sodium zirconium lactate. Further, the element zirconium has been reported to be retained in the osteoid fraction of bone. Because the tooth does not contain an osteoid fraction, the element zirconium is not necessarily retained within the hard tissues of the tooth. Thus, biologically, zirconium silicate is essentially non-reactive and non-toxic and thus a viable candidate for use in dental materials as is evident from its use as a polishing agent.

It is desired to provide various compositions of glass ionomer cements which are varied in terms of its color, viscosity and setting time to meet the particular application for which the cement is intended. It is also desired to provide glass ionomer cement that may be used as a restorative material, a cement for affixing a prosthesis, or a luting agent, base or liner. It is further desired to provide an additive to glass ionomer cement which may be added to any glass ionomer cement composition for any application in varying amounts to affect the characteristics of the cement without affecting the cement's intended functionality. Further, since some glass ionomer cement additives create a desired result in certain respects, such as the reduction of pupal sensitivity by neutralizing the cement's pH level through the addition of zinc oxide to the cement, but also create undesired results in other respects, it is desired to provide a mechanism by which the consequential affects of such an additive may be neutralized or negated.

SUMMARY OF THE INVENTION

These problems are overcome by providing an improved glass ionomer cement having an additive which allows one to control the color, mixability, and handling characteristics of the glass ionomer cement. The additive is believed inert to glass ionomer cement as it does not chemically react with the cement and because of this it is expected that a cement containing the additive is less soluble.

The invention comprises, in one form thereof, a dental composition comprising a glass ionomer cement, and an effective amount of is zircon additive to whiten the hardened glass ionomer cement. The invention comprises in other forms thereof, a dental composition comprising a glass ionomer cement and an effective amount of a zircon additive to selectively adjust the cement's viscosity and its setting time. The additive may comprise zircon crystals to effect the desired characteristics for cements intended for use as a restorative material, a cement for a prosthesis, such as a crown or bridge, or a luting agent or base or liner. The additive may also be combined with other known additives in controlling amounts to produce other desirable effects, such as the addition of zinc oxide to the improved glass ionomer cement to reduce pulpal sensitivity.

Accordingly, it is an advantage of the present invention to provide an additive for glass ionomer cements which allows one, through control of the amount of additive present, to control the color of the glass ionomer cement.

It is another advantage of the present invention to provide an additive for glass ionomer cements which permits one to control the handling characteristics of the cement by controlling the amount of additive present in the cement.

It is still another advantage of the present invention to be able to control the setting time of a glass ionomer cement by controlling the amount of an additive to the glass ionomer cement.

It is yet another advantage of the present invention to provide is an additive to glass ionomer cement which does not inhibit the functionality of the cement as it does not chemically react with the cement.

It is another advantage of the present invention to provide a glass ionomer cement additive that may be mixed with either the powder component or the liquid component of the cement.

It is still another advantage of the present invention to provide an additive that may be utilized with various glass ionomer cement compositions including those cements containing other additives or those cements utilized for a particular purposes, including restorative cements, cements for prostheses and cements utilized for luting or as a base or a liner.

DETAILED DESCRIPTION

It is known in the art that zircon, also known as zirconium silicate and zirconium silicon oxide ($ZrSiO_4$), when introduced in modest amounts, is biocompatible in both the intraoral and internal environments. It is also generally insoluble in tissue, bone and body fluids. Thus, it not only is viable for use as a prophylactic polishing agent as currently used, it may also be considered for other purposes wherein the composition including zircon may reside within the patient's mouth or inside the body. As shown by the Examples below, zircon has been found to be a viable additive to glass ionomer cements, allowing one to control the resultant color, viscosity and setting time of the cement without affecting the intended functionality of the cement. Zircon is essentially inert to glass ionomer cements, i.e., it does not interact with the other constituents of glass ionomer cement so as to modify the glass ionomer's delicate chemical balance.

To illustrate the affects of zircon on the color, viscosity and setting reactions of glass ionomer cement, tests were performed to compare the effects of the zircon additive to the effects of other known additives, namely zinc oxide, zirconia and silver alloy amalgam powder particles in a glass ionomer cement composition. For all tests performed, Shofu Type I GlasIonomer cement distributed by Shofu Dental Corporation of Menlo Park, California, the composition of which is provided herein above, was utilized. The silver alloy amalgam powder additive constituted the powder component of Sybraloy amalgam available from Kerr Manufacturing Company of Romulus, Michigan. Zirconium silicon oxide (zircon) crystals were obtained from Johnson Matthey Catalog Company of Ward Hill, Massachusetts, and constituted crystals of less than 1 micron; the zinc oxide utilized was obtained from Hooks Drug Stores and was packed by Humco Laboratory of Texarkana, Texas; and the zirconia was obtained from Zirconia Sales (America), Inc. of Marietta, Georgia. Both zinc oxide and zirconia were introduced in particulate form while the zircon additive comprised crystals of 1 micron or less. In each of Examples 2-5 the specified additive was first mixed with the powder component of the Shofu Type I Glass Ionomer cement to obtain the compositions specified in Tables 1-3 below. In Examples 6-8, the specified additive blend was added to the glass ionomer powder component. Next, the powder component containing the additive(s) and the liquid component of the Shofu Type I Glass Ionomer cement were mixed as directed by the manufacturer for thirty seconds. The tests were performed at a constant temperature of 68° F.

There are many instances in which the glass ionomer cement may be visible and therefore it is desirable to produce a cement which, when hardened, closely matches the color of the object to which the cement is adhered. Because the cement is often placed directly on a tooth, it is desirable to produce a white or off-white hardened cement.

To determine the effect of each additive on the color of the hardened glass ionomer cement, the mixtures were allowed to harden for twenty-four hours. The color of the hardened mixture was determined through the use of the Vita Lumin-Vacuum shade guide VMK 68 manufactured by Vita Zahnfabrik of Germany. The colors of the compositions tested are shown in Table 1 as follows:

TABLE 1

| Example | Additive(s) | % By Weight of Powder | Vita Color Scale | Color Description |
|---|---|---|---|---|
| 1 | None | | 540 | Cream |
| 2 | Zircon | 10% | 672 | White |
| 3 | Zinc Oxide | 10% | 537 | Light Cream |
| 4 | Zirconia | 10% | 565 | Flat White |
| 5 | Amalgam Alloy | 10% | 675 | Black |
| 6 | Zircon | 10% | 672 | White |
|   | Zirconia | 5% | | |
|   | Zinc Oxide | 5% | | |
| 7 | Zinc Oxide | 5% | 557 | Gray |
|   | Zirconia | 3% | | |
|   | Amalgam Alloy | 2% | | |
| 8 | Zircon | 5% | 537 | Light Cream |
|   | Zinc Oxide | 5% | | |

The results of color test for these Examples indicate that zircon additive whitens the glass ionomer cement and is therefore desirable in those applications of glass ionomer cement where the glass ionomer cement is to closely match that of white enamel or porcelain as zircon whitens the cement's color. Further, it has been shown that zircon may be used in combination with other additives to achieve the desired color.

The handling characteristics of a wet glass ionomer cement are of importance in its application to a lesion. If the mixture is too thick, it will be difficult to apply and may even be inclined to remain on the application instrument rather than "flowing" onto the lesion. Also, if the mixture is too thin, the cement may have the tendency to flow from the application instrument before being applied to the lesion, or, once on the lesion, a thin cement may tend to run off the surface to which the cement is to be applied. To measure the handling characteristics as reflected in the thickness of the cement, a simple "peak" test which is reflective of viscosity, was performed on each of the glass ionomer cement compositions. Specifically, after a composition was mixed, a mixing stick was dipped into the mixture and withdrawn. This dipping was repeated at regular time intervals until the peak formed from the withdrawal of the mixing stick held its shape as a peak for 5 seconds. The time required for the mixture to harden to a point at which the peak held its shape for at least 5 seconds was recorded. The test was continued until the peak formed by the withdrawal of the mixing stick remained permanently in place. The time period it takes for a peak to be formed which holds its shape for the specified time periods serves as an indication of the mixture's viscosity. The longer it takes to form a peak which holds its shape, the thinner the mixture. The results of these tests are shown in Table 2 below (all times noted as minutes:-seconds):

TABLE 2

| Example | Additive(s) | % By Weight of Powder | 5 Second Peak | Permanent Peak |
|---|---|---|---|---|
| 1 | None | | 2:45 | 4:15 |
| 2 | Zircon | 10% | 4:00 | 6:20 |
| 3 | Zinc Oxide | 10% | 0:05 | 0:15 |
| 4 | Zirconia | 10% | 2:10 | 4:30 |
| 5 | Amalgam Alloy | 10% | 1:45 | 3:30 |
| 6 | Zircon | 10% | 1:05 | 2:00 |
|   | Zirconia | 5% | | |
|   | Zinc Oxide | 5% | | |
| 7 | Zinc Oxide | 5% | 0:45 | 1:40 |
|   | Zirconia | 3% | | |
|   | Amalgam Alloy | 2% | | |
| 8 | Zircon | 5% | 0:50 | 3:30 |
|   | Zinc Oxide | 5% | | |

It is evident that the zinc oxide and amalgam alloy additives requires less time to create and maintain a peak, with zinc oxide requiring the least time. Thus, zinc oxide and amalgam alloy additives essentially result in a thicker mixture which hardens rapidly and therefore may be unsuited for certain applications. When zircon is used as an additive, a longer period of time is necessary to create and maintain a peak. As a result, when zircon additive is used, the mixture created is thinner than a cement which does not contain the additive. Thus, it was observed that the glass ionomer cement with zircon additive only (Example 2) was easy to mix and very smooth, while the glass ionomer cement with zinc oxide additive only (Example 3) was hard to mix, stiff and seemingly unsuitable for many applications. The presence of only zirconia as an additive (Example 4) had the least effect on the viscosity and handling characteristics of an unmodified glass ionomer cement.

It will be appreciated by those of skill in the art that zircon alone may be added to glass ionomer cement to reduce the thickness of a cement. Alternately, zircon may be added in combination with other additives. The zinc oxide and amalgam alloy additives all create a thicker mixture. Therefore, if one wishes to affect a characteristic of the cement other than thickness by adding one of these additives, the thickening affect of the additive may be neutralized or negated by the addition of zircon to the mixture. For example, when zinc oxide is added to the cement to reduce pulpal sensitivity by neutralizing the cement's pH, the resulting mixture may be too thick for some applications. Thus, zircon may also be added to the cement to counteract the thickening consequence of adding is zinc oxide as illustrated by comparing the results of Examples 1, 3 and 8.

Another characteristic of glass ionomer cement of importance in the application for which the cement is to be utilized is setting time, i.e., the time it takes for the cement to be substantially hardened. Some applications, such as the use of the cement for affixing a prosthesis, require a relatively long setting time to permit the dentist to perform other tasks while the cement hardens. In other applications, such as the use of the cement as a base, it is desirable to use a fast setting cement. Though intuitively one might conclude that there exists a direct correlation between thickness of the glass ionomer cement and its setting time, this is not the case. For example, a cement which appears relatively thick shortly after mixing the powder and liquid components may take longer to completely harden than would a thinner mixture. The hardening process is dynamic as it depends on the chemical reactions occurring in the cement. Practically speaking, a dentist may desire a thick, slow setting glass ionomer cement for use in affixing a prothesis: thickness providing the means by which a substantial amount of cement may be adhered to the lesion and slow setting to permit sufficient time for the dentist to perform the necessary procedure.

To determine the effect of zircon on the setting time of the glass ionomer cement in comparison to the setting time of glass ionomer cements containing other additives or additive blends, pressure from a mixing stick applied to the mixture was repeated until the hardened mixture cracked from the application of such force. It should be noted that prior to hardening, the pressure exerted by the mixing stick would either leave an impression on the mixture indicating that the mixture was still soft, or would essentially have no effect. The setting times for the various Examples determined from this test are shown in Table 3 as follows:

TABLE 3

| Example | Additive(s) | % By Weight of Powder | Setting Time (min:sec) |
|---|---|---|---|
| 1 | None | | 14:25 |
| 2 | Zircon | 10% | 20:00 |
| 3 | Zinc Oxide | 10% | 14:30 |
| 4 | Zirconia | 10% | 15:30 |
| 5 | Amalgam Alloy | 10% | 9:55 |
| 6 | Zircon | 10% | 15:30 |
|   | Zirconia | 5% | |
|   | Zinc Oxide | 5% | |
| 7 | Zinc Oxide | 5% | 10:30 |
|   | Zirconia | 3% | |
|   | Amalgam Alloy | 2% | |
| 8 | Zircon | 5% | 15:40 |
|   | Zinc Oxide | 5% | |

The addition of zircon to glass ionomer cement in the amount of 10% by weight of the powder component of the cement (Example 2) substantially increased the setting time of the glass ionomer cement. Zinc oxide (Example 3) and zirconia (Example 4) additives essentially had no effect on the setting time of the cement. The amalgam powder additive (Example 5) substantially reduced the setting time of the glass ionomer cement. It is interesting to note that although the zinc oxide additive resulted in a much thicker mixture, as previously discussed, the setting time for this mixture was not substantially less than the setting time of glass ionomer cement containing no additives. Since zinc oxide chemically reacts with the glass ionomer cement, "thicker" does not necessarily mean dryer and thus a shorter setting time. On the other hand, it is surmised that there may be a more direct comparison between thickness of the mixture and its setting time for the zircon additive as zircon is inert to glass ionomer cement.

The results of these tests can be summarized by the following representations of continuums of various characteristics of the glass ionomer cement:

| Color | | | |
|---|---|---|---|
| Darkest Amalgam alloy | Zinc oxide | Zirconia | Lightest Zircon |
| Viscosity | | | |
| Thinnest Zircon | Zirconia | Amalgam alloy | Thickest Zinc Oxide |
| Setting Time | | | |
| Fastest Amalgam alloy | Zinc oxide | Zirconia | Slowest Zircon |
| Ease of Mixing | | | |
| Most difficult Zinc Oxide | Zirconia | Amalgam alloy | Easiest Zircon |

As is evident from these results zircon when compared to zinc oxide, zirconia and amalgam alloy as an additive to glass ionomer cement, has significant effects on the color, thickness and setting times of the glass ionomer cement.

Of concern with an additive to a dental composition intended to modify at least one of the characteristics of the cement is the effect that additive may have on other characteristics. For example, although an additive may be desirable for the modification of the cement's color, thickness (viscosity) and setting time, the additive may be of little value or use if its presence reduce the bond strength of the cement. Zircon is inert to glass ionomer cement and therefore may be anticipated as not interfering with the chemical bonding of the cement to an object; however, it is plausible that its presence may nonetheless have a mechanical bonding effect or that it may interact in some manner with the object(s) to which glass ionomer cement is applied. To examine the bond strength of the glass ionomer cements containing various additives, including zircon, pull strength tests were performed using various glass ionomer cement compositions.

As previously mentioned, one use of glass ionomer cement is disclosed in U.S. patent application Ser. No. 07/942,375, filed Sep. 9, 1992, wherein a layer of wet glass ionomer cement is applied to a prepared lesion in a living tooth and a layer of wet amalgam is placed on the layer of cement before the cement is allowed to harden. As in U.S. application Ser. No. 07/942,375, pull strength tests were performed to measure the is bond strength of wet glass ionomer cement to wet amalgam. Specifically, each of the various compositions of glass ionomer cements listed in Table 4 were created by mixing the additives, if any, in the quantities specified, with the glass ionomer powder prior to mixing the powder with the glass ionomer liquid. Sybraloy amalgam, available from Kerr Manufacturing Company of Romulus, Michigan, was mixed according to the manufacturer's instructions. For each Example, assemblies each comprised of wet amalgam, wet glass ionomer cement and wet amalgam were formed with plastic capsules. The plastic was of a type which does not adhere to glass ionomer cement. Therefore, undercuts were made into the plastic capsules to form mechanical retention of the amalgam within the capsule. Care was taken in the building of these assemblies to use the same quantity of materials in each assembly and to limit the amount of force used to apply each layer. The assemblies were then allowed to harden for 24 hours. One end of the assembly, a capsule comprising hardened amalgam was clamped to a fixed table surface and the other end of the assembly, also comprising hardened amalgam in a capsule, was attached to a scale. Weights were then added to the scale until the plug broke apart at the interface between the glass ionomer cement and one or both of the hardened amalgam layers. Ten (10) sample sandwich assemblies of each glass ionomer cement composition were tested in this manner and the results averaged for each composition. The results of the pull strength test for various glass ionomer (GI) cement compositions are shown in Table 4 as follows:

TABLE 4

| Description of Cement | Strength (PSI) |
|---|---|
| GI only | 135 |
| GI w/10% Zircon | 197 |
| GI w/5% Zircon + 5% Zinc Oxide | 220 |
| GI w/3% Zircon + 5% Zinc Oxide | 216 |
| GI w/20.6% Zircon + 20.6% Zirconia | 207 |
| GI w/10% Zircon + 10% Zirconia | 218 |

The results of the pull strength tests indicate that the presence of the zircon additive, either alone or in combination with other additives, not only did not adversely affect bond strengths, but instead resulted in bond strengths that are far superior to those measured without the additive. By adding zircon alone to the glass ionomer cement such that the zircon comprised 10% by weight of the glass ionomer powder, pull strengths increased 62 PSI from 135 PSI to 197 PSI, a 46% increase in the bond strength. It is noteworthy that the presence of other additives, namely zinc oxide and zirconia, in addition to the additive zircon resulted in even higher pull strength tests results. Thus, the zircon additive, in the combinations considered herein, is desirable as its presence improves the bond strength of wet glass ionomer cement to wet amalgam after both the cement and the amalgam have hardened.

In many instances, the presence of the zircon crystals may be used to offset a change to the characteristics of the cement caused by the introduction of an additive which chemically interacts with the cement composition to create one or more desirable affects. For example, addition of zinc oxide to the glass ionomer cement is desirable in that it is known to reduce pulpal sensitivity by neutralizing the cement's pH. However, the zinc oxide additive also significantly changes the handling characteristics of the cement which may cause problems in certain applications. By adding zircon crystals with the zinc oxide, the handling characteristics may be neutralized.

The zircon crystal additive does not interact with either the glass ionomer powder component or the glass ionomer liquid component, either alone or in combination. In experimenting with varying amounts of zircon additive, the additive has been added in amounts from a trace, 0.01% by weight of the cement, up to about 33% by total weight of the cement. When the zircon level approaches 33% of the total weight of the cement, the cement becomes impractical for use as it is very thin and has a very long and unreasonable setting time. Within an acceptable range of about 0.01% to about 33% by weight, mixtures were prepared in which the zircon was added to the powder component of the glass ionomer cement, and to the liquid component of the glass ionomer cement. No appreciable differences resulted based on the method used to include the zircon additive in the cement.

In exploring variations on the composition of a glass ionomer cement having the zircon crystal additive, certain compositions are known to work well with Shofu Type I Glass ionomer cement when used in conjunction with the method for filing a restoration as disclosed in U.S. patent application. Ser. No. 07/942,375, filed Sep. 9, 1992, and which is incorporated herein by reference. Shofu type I Glass ionomer cement's powder component consists of 20-30% silica, 1-10% boron oxide, 10-20% aluminum oxide, 1-10% ammonium fluoride, 1-10% phosphorus pentoxide and 1-5% calcium fluoride. Shofu type I glass ionomer cement's liquid component consists of 100-80% by weight of polyacrylic acid of low molecular weight, 40% solution in water, and 0-20% by weight of d-tartaric acid. The powder component is mixed with the liquid component in a ration of 1:1 to 2:1 by weight. As previously stated, the addition of zircon crystals from about 0.01% to about 33% by weight of the total cement yield a usable cement, although setting times become unreasonably high when higher levels are added in excess of 33%. A preferred handling composition comprised the addition of the zircon additive of approximately 10% by weight of the powder component. A preferred cement having color matching that of dentin and having desirable handling characteristics comprised additives of zinc oxide (5% by weight of the powder component), zirconia (5% by weight of the powder component) and zircon (10% by weight of the powder component).

It will be appreciated by those of skill in the art that the is particular amount of zircon crystals added to the glass ionomer cement is dependent on the intended results of the additive with respect to the color, handling characteristics and setting time desired for a particular application. In addition, various glass ionomer cements may exhibit different handling characteristics, color and setting time due to differences in their own chemical makeup. For example, Ketac-CEM Radiopaque glass ionomer cement distributed by ESPE Premier Sales corp. of Norristown, Pennsylvania, handles differently and has a setting time different from that of Shofu Type I Glass Ionomer cement. The particular amount of zircon crystals to be added to a particular glass ionomer cement to obtain the desired effects of the additive may therefore vary depending upon the chemical makeup of the glass ionomer cement. For example, it was found that the desired changes in color, handling and setting time could be obtained using lesser amounts of zircon with the Ketac-CEM Radiopague cement than with the Shofu Type I cement. The precise difference will of course vary with the particular cement used; however, such adjustment may be readily accomplished without undue experimentation by those of skill in the art.

The particle sizes of the constituents of a glass ionomer cement powder to be utilized as a restorative material differ, preferably are larger (greater than 10 microns), than the particles (5 to 10 microns) used in glass ionomer cements intended as a luting agent or a base or a liner. Thus, the size of the zircon crystals added to glass ionomer restorative materials need not be limited to 1 micron or less in all cases. Rather, crystal sizes of up to 20-30 microns may work well in a restorative material. Alternately, crystals of varying sizes may be utilized.

It is quite feasible that zircon may be used as an additive in other cements used in both the dental and medical fields. For example, it may be desired to modify the color, handling and setting times of polycarboxylate cements used in dentistry. Polycarboxylate cements are created by mixing a powder component, usually containing zinc oxide and magnesium sulfate and often, stannous fluoride, with a liquid component comprising an aqueous solution of polyacrylic acid. Principally, the effect of the presence of the zircon is the same, i.e., it does not chemically react with the polycarboxylate cement, and it is biocompatible and insoluble.

It is also possible that zircon may be added to other cements used in the medical or dental fields. For example, zircon may be added to a cement composition used to adhere an implant to bone, bone to bone, synthetic bone to an implant, etc. Again, introduction of the zircon crystals to the cement may allow one to control the color, handling and setting time of such a cement whether intraoral or internal.

What is claimed is:

1. A tooth restoration comprising:
   a layer of glass ionomer cement bonded to the tooth, the glass ionomer cement comprising
      a powder component and a liquid component, and zircon; and
   a layer of amalgam disposed on the layer of glass ionomer cement,
   the restoration being formed by the process of applying a layer of wet glass ionomer cement to a tooth lesion, placing a layer of wet amalgam directly on the layer of wet glass ionomer cement, and allowing the cement and the amalgam to harden to thereby bond the amalgam to the tooth.

2. The restoration of claim 1 wherein said zircon comprises from about 0.01% to about 33.0% by weight of the total weight of said composition.

3. The restoration of claim 1 wherein said zircon is included with either said powder component or said liquid component prior to mixing of said component with said other component to form said dental restoration.

4. The restoration of claim 3 wherein said zircon comprises from about 0.01% to about 20% by weight of said glass ionomer powder component when said zircon is included with said powder component.

5. The restoration of claim 3 wherein zircon comprises from about 0.01% to about 15% by weight of said glass ionomer liquid component when said zircon is included with said liquid component.

6. The restoration of claim 3 wherein said powder component of said glass ionomer cement comprises particles of about 5 microns to about 10 microns and wherein said zircon comprises crystals of 1 micron or less.

7. The restoration of claim 3 wherein said powder component of said glass ionomer cement comprises particles greater than 10 microns and wherein said zircon comprises crystals from less than 1 micron to about 30 microns.

8. The restoration of claim 1, further comprising:
   zinc oxide comprising from about 0.01% to about 20% by weight of said powder component of said cement; and
   wherein said zircon comprises from about 0.01% to about 20% by weight of said powder component of said cement.

9. The restoration of claim 8, further comprising:

zirconium oxide comprising from about 0.01% to about 20% by weight of said powder component of said cement.

10. The restoration of claim 1, further comprising:
amalgam powder comprising from about 0.01% to about 20% by weight or said powder component of said cement; and wherein the zircon comprises from about 0.01% to about 20% by weight of the powder component of the cement.

* * * * *